United States Patent
Zhang et al.

(10) Patent No.: US 8,020,992 B2
(45) Date of Patent: *Sep. 20, 2011

(54) HUMAN EYE ADAPTIVE OPTICAL VISUAL PERCEPTION TRAINING METHOD AND APPARATUS THEREOF

(75) Inventors: Yudong Zhang, Sichuan (CN); Yifeng Zhou, Anhui (CN); Yun Dai, Sichuan (CN); Xuejun Rao, Sichuan (CN); Haoxin Zhao, Sichuan (CN)

(73) Assignees: The Institute of Optics and Electronics, The Chinese Academy of Sciences, Chengdu, Sichuan (CN); University of Science and Technology of China, Hefei, Anhui (CN)

( * ) Notice: Subject to any disclaimer, the term of this patent is extended or adjusted under 35 U.S.C. 154(b) by 26 days.

This patent is subject to a terminal disclaimer.

(21) Appl. No.: 12/794,511

(22) Filed: Jun. 4, 2010

(65) Prior Publication Data

US 2011/0149238 A1 Jun. 23, 2011

(30) Foreign Application Priority Data

Dec. 18, 2009 (CN) .......................... 2009 1 0262470

(51) Int. Cl.
*A61B 3/00* (2006.01)
*A61B 3/10* (2006.01)
(52) U.S. Cl. .......................... 351/203; 351/200; 351/211
(58) Field of Classification Search .................. 351/203, 351/200, 205, 210–212, 221
See application file for complete search history.

(56) References Cited

U.S. PATENT DOCUMENTS

| | | | |
|---|---|---|---|
| 2003/0147048 A1* | 8/2003 | Mihashi | 351/211 |
| 2008/0284979 A1* | 11/2008 | Yee et al. | 351/209 |
| 2010/0073469 A1* | 3/2010 | Fateh | 348/62 |

OTHER PUBLICATIONS

Williams, David R., et al., "Formation and Acquisition of the Retinal Image"; In: J.S.W. Leo M. Chalupa (Ed.) The Visual Neurosciences, The MIT Press, Cambridge, Massachusetts, London, England (2003); pp. 795-810.

Yoon, Geun-Young, et al., "Visual performance after correcting the monochromatic and chromatic aberrations of the eye"; J. Opt. Soc. Am. A/vol. 19, No. 2 (Feb. 2002); pp. 266-275.

Chiu, Chiayu, et al., "The Role of Neural Activity in the Development of Orientation Selectivity"; In: J.S.W. Leo M. Chalupa (Ed.) The Visual Neurosciences, The MIT Press, Cambridge, Massachusetts, London, England (2003); pp. 117-125.

(Continued)

*Primary Examiner* — Dawayne A Pinkney
(74) *Attorney, Agent, or Firm* — Osha • Liang LLP

(57) ABSTRACT

The present invention proposes a human eye adaptive optical visual perception training apparatus, comprising: a human eye wave aberration measurement sub-system for measuring the human eye wave aberration of a person to be tested; a human eye wave aberration correction sub-system for driving and controlling the wavefront corrector to correct the human eye wave aberration of the person to be tested based on the measured human eye wave aberration of the tested person; and a visual perception training sub-system for processing and displaying sighting targets of different spatial frequencies and different contrasts, and presenting the sighting targets to the tested person, to conduct a human eye visual function measurement process and a visual perception training process. The apparatus according to the present invention is capable of several functions including eye aberration correction, visual function measurement, visual perception training. Finer visual stimulus is obtained by correcting human eye aberration, and then the human eye acuity limit can be measured, and the visual perception training effect and visual function of the human eye can be efficiently improved by performing visual perception training with such apparatus.

9 Claims, 2 Drawing Sheets

OTHER PUBLICATIONS

Zhou, Yifeng, et al., "Perceptual learning improves contrast sensitivity and visual acuity in adults with anisometropic amblyopia"; Vision Research 46 (2006); pp. 739-750.

Marcos, Susana, et al., "Influence of adaptive-optics ocular aberration correction on visual acuity at different luminances and contrast polarities"; Journal of Vision (2008) 8(13):1; ISSN 1534-7362; doi; 10.1167/8.13.1; pp. 1-12.

* cited by examiner

HUMAN EYE ADAPTIVE OPTICAL VISUAL PERCEPTION TRAINING METHOD AND APPARATUS THEREOF

BACKGROUND OF THE INVENTION

1. Field of Invention

The present invention relates to a human eye adaptive optical visual perception training method and a training apparatus capable of several functions including eye aberration correction, visual function measurement (including but not limited to a contrast threshold measurement), visual perception training. Finer visual stimulus is obtained by correcting human eye aberration by means of an adaptive optical system, and then the human eye acuity limit can be measured, and the visual perception training effect and visual function of the human eye can be efficiently improved by performing visual perception training with such apparatus.

2. Description of Prior Art

The development of vision of human is a progressive process. The eyeballs have grown to a certain extent when a person is born. However, the growing is not full in terms of anatomy or physiological function, and the eyeballs will continue growing in a long term thereafter. The normal development of Vision requires two conditions, one is the postnatal developing processing, and the other is external visual stimulus. Ages 0-7 are the golden stage for vision development, during which if the eyes are shaded for a long time, the vision will not develop and remain at a low level due to deficiency of normal visual stimulus from external images.

The function of the eyeballs is dominant for the vision of a person. Usually, an eyeball has no so perfect optical characteristic and whose capability is affected by various factors including, for example, diffraction of pupil, aberration from cornea and lens and dispersion of aqueous humor (R. Williams, D., & Hofer, H., Formation and Acquisition of the Retinal Image. In: J.S.W. Leo M. Chalupa (Ed.) The Visual Neurosciences, the MIT Press, Cambridge, Mass., London, England, 2003).

Generally, the effect due to the dispersion of aqueous humor is so small that is negligible. The aberration is large while the diffraction is small if the pupil becomes large, whereas the aberration is small while the diffraction is large if the pupil becomes small. The aberration of human eyes includes low-order aberration and high-order aberration, the former can be easily corrected but the latter is difficult to be corrected.

Recently, many researchers (Geun-Young Yoon and David R. Williams, Visual Performance after correcting the monochromatic and chromatic aberrations of the eye, J. Opt. Soc. Am. A/Vol. 19, No. 2) attempt to apply the Adaptive Optics technology in the research of vision to explore the relationship between the high-order aberration and normal vision and to explore the limit for spatial vision. However, it is not agreed whether a supernormal vision can be reached after all the aberration (including the low order and the high order) of a visual system are corrected (Marcos, S., Sawides, L., Gambra, E., & Dorronsoro, C., Influence of adaptive-optics ocular aberration correction on visual acuity at different luminances and contrast polarities. 8: 1-12, 2008).

A visual system can only correctly develop with the aid of visual experiences (Chiu, C., & Weliky, M., The Role of Neural Activity in the Development of Orientation Selectivity. In: J.S.W. Leo M. Chalupa (Ed.) The Visual Neurosciences, The Mit Press, Cambridge, Mass., London, England, 2003). The development of a fine acuity needs the fine development of the visual nervous system which depends on clarity degree of imaging on the retina for the optical system of an eyeball. An image cannot be clearly generated on the retina due to the high-order aberration and dispersion. The spatial cut off frequency that can be differentiated by the visual nervous system will be no larger than the highest spatial frequency of the image generated on the retina by the eyeballs.

The visual perception leaning process shows that the identification capability of the nervous system for a certain image will be largely improved via learning, which indicates that the nervous system is trainable even for an adult. Many psychological tests reveal that an adult can increase his success ratio and speed for a lot of visual perception tasks by learning (Zhou Y F, Huang C B, Xu P J, Tao L M, Qiu Z P, Li X R and Lu Z L, Perceptual Learning Improves Contrast Sensitivity and Visual Acuity in Adults with Anisometropic Amblyopia. Vision Research, 46(5): 739-750, 2006). However, the prior visual perception learning process uses eyeglass to correct the low-order aberration, and an image cannot be clearly generated on the retina due to the still existed high-order aberration and dispersion. Accordingly, the simple visual perception leaning process improves the visual function to an extent limited by the clarity of the image.

In view that the visual nervous system is trainable, the present invention combines the adaptive optical aberration correction technique and the visual perception learning technique. The quality of the image generated on the retina can be largely improved after the aberration is corrected through the adaptive optical technique. If the visual perception leaning process is conducted with such fine visual stimulus, the acuity of the visual nervous system can be enhanced, and thereby the visual perception training effect and visual function of human eyes can be efficiently improved.

SUMMARY OF THE INVENTION

In view of above disadvantages in the prior arts, the present invention proposes a human eye adaptive optical visual perception training method and an apparatus capable of several functions including eye aberration correction, visual function measurement (including but not limited to a contrast threshold measurement), visual perception training. Finer visual stimulus is obtained by correcting eye aberration by means of an adaptive optical system, and then the eye acuity limit can be measured, and the visual perception training effect and visual function of human eyes can be efficiently improved by performing visual perception training with such apparatus.

According to the first aspect of the present invention, there is proposed a human eye adaptive optical visual perception training method, comprising the step of: a human eye wave aberration measurement step for measuring the human eye wave aberration of a person to be tested by using a near infrared reference light source, a wavefront corrector and a wavefront sensor; a human eye wave aberration correction step for driving and controlling the wavefront corrector to correct the human eye wave aberration of the person to be tested based on the measured human eye wave aberration of the tested person; and a visual perception training step for displaying on a sighting target display sighting targets of different spatial frequencies and different contrasts after they have been subjected to processing in a video processing circuit, and presenting the sighting targets to the tested person via the driven and controlled wavefront corrector, to conduct a human eye visual function measurement process and a visual perception training process.

Preferably, the human eye visual function measurement process consists in a human eye contrast threshold measurement, where the difficulty of the stimulus is adjusted in real time in response to the reply from the tested person according to the adjustment method of psychophysics. The contrast of the sighting target to be displayed next is decreased if the number of continuous replies from the tested person that are correct reaches a first predetermined value, and the contrast is increased if the number of continuous replies that are wrong reaches a second predetermined value. The correctness of the tested person during the whole measurement process maintains at a level though the adjustment and then a human eye contrast threshold of the tested person is obtained. A human eye contrast sensitivity is obtained by reversing the human eye contrast threshold. More preferably, the visual perception training process comprises steps of: measuring a human eye contrast threshold of the tested person respectively for gratings of different spatial frequencies; selecting a spatial frequency corresponding to a predetermined human eye contrast threshold based on the difference of the contrast thresholds under different spatial frequencies; and conducting the visual perception training process by using the grating with the selected spatial frequency.

Alternatively, the visual perception training process comprises steps of: selecting the spatial frequency measured after the preceding visual perception training process; and conducting the visual perception training process by using the grating with the selected spatial frequency.

According to the second aspect of the present invention, there is proposed a human eye adaptive optical visual perception training apparatus, comprising: a human eye wave aberration measurement sub-system including a near infrared reference light source, a wavefront corrector and a wavefront sensor, for measuring the human eye wave aberration of a person to be tested; a human eye wave aberration correction sub-system including a control unit and said wavefront corrector, for driving and controlling the wavefront corrector to correct the human eye wave aberration of the person to be tested based on the measured human eye wave aberration of the tested person; and a visual perception training sub-system including a video processing circuit, a sighting target display and said wavefront corrector, for displaying on the sighting target display sighting targets of different spatial frequencies and different contrasts after they have been subjected to processing in the video processing circuit, and presenting the sighting targets to the tested person via the driven and controlled wavefront corrector, to conduct a human eye visual function measurement process and a visual perception training process.

Preferably, the wavefront corrector is selected from a group consisted of a deformable reflective mirror, a liquid crystal wavefront corrector, a Micromachined membrane deformable mirror, a Microelectromechanical deformable mirror, a is Bimorph deformable mirror, and a liquid deformable mirror.

Preferably, the wavefront sensor is selected from a group consisted of a microlens-array-based Hartmann wavefront sensor, a microprism-array-based Hartmann wavefront sensor, a Curvature wavefront sensor and a Pyramid wavefront sensor.

Preferably, the sighting target display is selected from a group consisted of a CRT display, a commercial display, a liquid crystal display, a plasma display, an electro-luminescent display, and an organic luminescent display. Preferably, the video processing circuit combines the R channel and the B channel from the normal video output and obtains a gray-scale of or higher than 14 bits.

Compared to the prior art, the present invention proposes the concept of applying the adaptive optical technology in the visual perception training process for the first time. The apparatus according to the present invention is capable of several functions including eye aberration correction, visual function measurement (including but not limited to a contrast threshold measurement), visual perception training. Compared with the prior visual perception training process, the apparatus can obtain fine visual stimulus by correcting eye aberration by means of an adaptive optical system, and then the eye acuity limit can be measured, and thereby the visual perception training effect and the visual function measurement of human eyes can be efficiently improved by performing visual perception training with such apparatus.

BRIEF DESCRIPTION OF THE DRAWINGS

The above and other objects, features and advantages of the present invention will be clearer from the following detailed description about the non-limited embodiments of the present invention taken in conjunction with the accompanied drawings, in which.

DETAILED DESCRIPTION OF PREFERRED EMBODIMENTS

Hereunder, the present invention will be described in accordance with the drawings. In the following description, some particular embodiments are used for the purpose of description only, which shall not be understood as any limitation to the present invention but the examples thereof. While it may blur the understanding of the present invention, the conventional structure or construction will be omitted.

Figure 1:
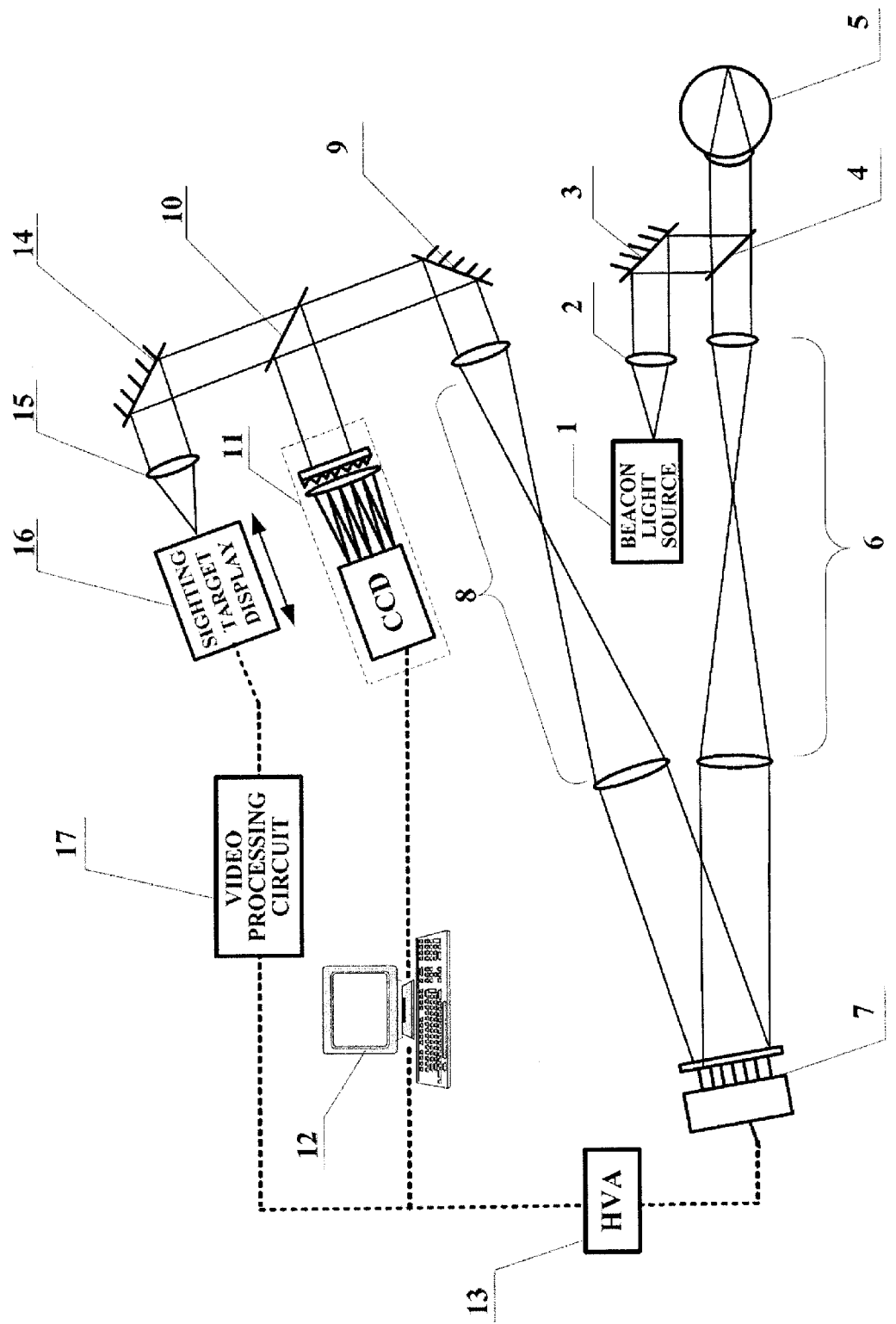
FIG. 1 is a schematic block diagram to show the respective units operating in the present invention.

FIG. 1 is a schematic block diagram to show the respective units operating in the present invention.

As shown in FIG. 1, a human eye adaptive optical visual perception training apparatus according to the present invention comprises a near infrared reference light source 1, a collimating lens 2, a first reflector 3, a first beam splitter 4, a beam matching afocal system 6, a wavefront corrector 7, a beam matching afocal system 8, a second reflector 9, a second beam splitter 10, a wavefront sensor 11, a computer 12, a high voltage amplifier 13, a third reflector 14, an imaging optical system 15, a sighting target display 16 and a video processing circuit 17. The human eye is denoted by the reference sign 5.

The human eye adaptive optical visual perception training method according to the present invention comprises following three stages: a human eye wave aberration measurement stage, a human eye wave aberration correction stage and a visual perception training stage.

At the human eye wave aberration measurement stage, the near infrared reference light source 1 emits lights, which are collimated by the collimator 2 and reflected by the first reflector 3 and the first beam splitter 4, and finally enter into the pupil of the human eye 5. The lights are reflected from the eyeground, travel through the beam matching afocal system 6 after reflection on the first beam splitter 4 and reach the wavefront corrector 7, which reflects the lights to the beam matching afocal system 8. The lights arrive at the wavefront sensor 11 after they are reflected from the second reflector 9 and the second beam splitter 10. The wavefront sensor 11 transmits the measured error signal to the computer 12 to obtain the human eye wave aberration.

Then at the human eye wave aberration correction stage, the computer 12 obtains the control voltage for the wavefront corrector 7 by running a computer control application based on the obtained human eye wave aberration. The control voltage is amplified by the high voltage amplifier 13 and applied on the wavefront corrector 7 to drive it, and thereby correcting the human eye wave aberration.

The visual perception training state starts after the human eye wave aberration correction stage. A visual function measurement and vision training application executed on the computer 12 generates sighting targets of different spatial frequencies and different contrasts. The generated sighting targets are displayed on the sighting target display 16 after they are subjected to processing in the video processing circuit 17. The person under test views the sighting targets displayed on the sighting target display 16 through the first beam splitter 4, the beam matching afocal system 6, the wavefront corrector 7, the beam matching afocal system 8, the second reflector 9, the second beam splitter 10, the third reflector 14 and the imaging lens 15. The visual perception training process and the human eye visual function measurement process (including but not limited to contrast threshold measurement) commence.

The wavefront corrector 7 may be selected from a group consisted of a deformable reflective mirror, a liquid crystal wavefront corrector, a Micromachined membrane deformable mirror, a Microelectromechanical (MEMS) deformable mirror, a Bimorph deformable mirror and a liquid deformable mirror.

The wavefront sensor 11 may be selected from a group consisted of a microlens-array-based Hartmann wavefront sensor, a microprism-array-based Hartmann wavefront sensor (see the Chinese Invention Patent No. ZL03126431.X), a Curvature wavefront sensor and a Pyramid wavefront sensor. The sighting target display 16 may be selected from a group consisted of a CRT display, a commercial display, a liquid crystal display, a plasma display, an electro-luminescent display, and an organic luminescent display.

The video processing circuit 17 may combine the R channel and the B channel from the normal video output and obtains a grayscale of or higher than 14 bits (corresponding to 16384 levels), to meet the requirements for the human eye visual function measurement process and the visual perception training process. For example, the video processing circuit 17 may take the form of a circuit as disclosed in the Chinese Utility Patent No. ZL02220968.9.

Figure 2:
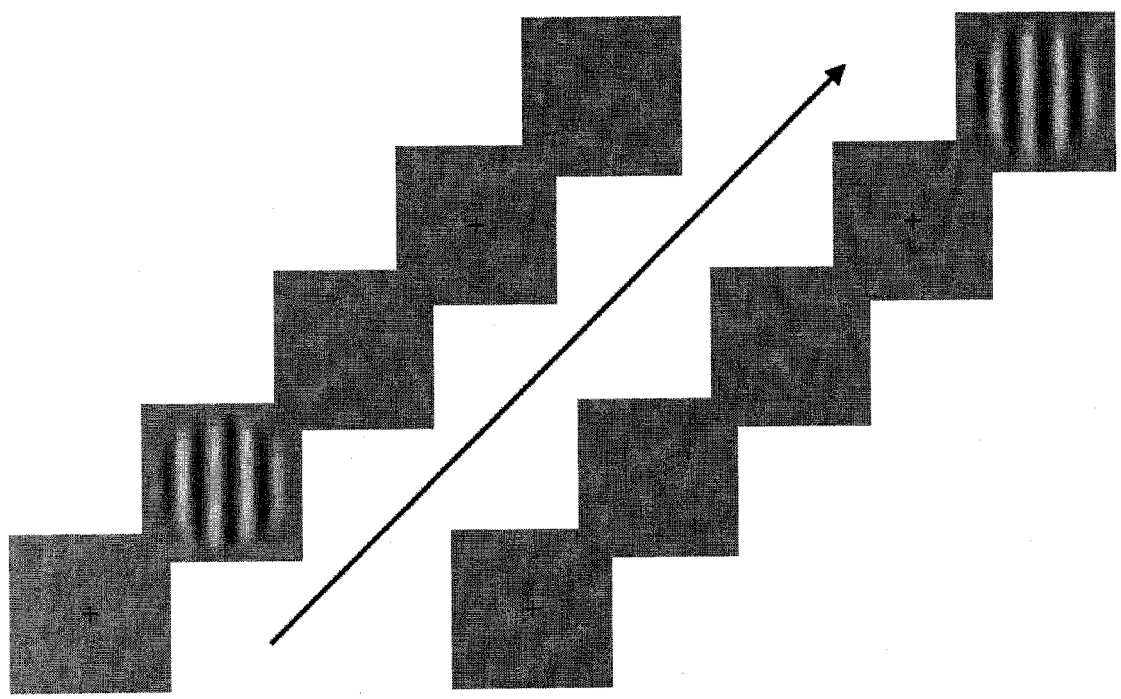
FIG. 2 is a schematic diagram to show the visual perception training process of the present invention.

FIG. 2 is a schematic diagram to show the visual perception training process of the present invention.

As shown in FIG. 2, during each training process, a crisscross appears on the screen two times sequentially, in company with an audio cue. Following each crisscross appearance, there may be presented a blank (a gray screen), or a target (i.e., a sinusoidal grating subjected to soft edge processing) to be detected. The person to be tested is required to press the left key to make a response when the grating appears after the crisscross occurs for the first time. The person is required to process the right key to make a response when the grating appears after the crisscross occurs for the second time. The process is repeated until all the training tasks, i.e., the tasks for the whole day, are completed.

In the present invention, the human eye visual function measurement process consists in a human eye contrast threshold measurement, where the difficulty of the stimulus is adjusted in real time in response to the reply from the tested person according to the adjustment method of psychophysics. The contrast of the sighting target to be displayed next is decreased, i.e., the difficulty is enhanced, if the tested person correctly responds continuously for three times. If the tested person wrongly responds, the contrast of the sighting target to be displayed next is increased, to lower the difficulty. By such adjustment, the correctness of the tested person during the whole measurement process maintains nearly unchanged. At the end, the contrast will converge to the human eye contrast threshold for the tested person. The human eye contrast sensitivity is obtained by reversing the human eye contrast threshold.

The visual perception training process can adopt the conventional "test→training→re-test" method, where the human eye contrast sensitivity curves before and after the visual perception training process are measured under eight spatial frequencies (including 0.6, 1, 2, 4, 8, 16, 24 and 32 cycles per degree) and the gratings of different spatial frequencies appear randomly. After the measurement, the contrasts of the eight spatial frequencies converge to the human eye contrast thresholds of the test person. An appropriate spatial frequency (i.e., the cut off frequency) is selected for training based on the difference of the human eye contrast thresholds under different spatial frequencies. For example, the spatial frequency corresponding to a human eye contrast threshold of 0.4 of a person is deduced according to a known contrast sensitivity curve. The visual perception training process requires the tested person to conduct the training tasks for a predetermined amount at the same time of each day under the selected spatial frequency. The training may adopt an adjustment method similar as the contrast threshold measurement, and automatically takes the contrast threshold finally obtained after the training of the previous day as the initial value for the next day, while the frequency of the grating maintains unchanged.

The foregoing description gives only the preferred embodiments of the present invention and is not intended to limit the present invention in any way. Thus, any modification, substitution, improvement or like made within the spirit and principle of the present invention should be encompassed by the scope of the present invention.

What is claimed is:

1. A human eye adaptive optical visual perception training method, comprising the step of:
   a human eye wave aberration measurement step for measuring the human eye wave aberration of a person to be tested by using a near infrared reference light source, a wavefront corrector and a wavefront sensor;
   a human eye wave aberration correction step for driving and controlling the wavefront corrector to correct the human eye wave aberration of the person to be tested based on the measured human eye wave aberration of the tested person; and
   a visual perception training step for displaying on a sighting target display sighting targets of different spatial frequencies and different contrasts after they have been subjected to processing in a video processing circuit, and presenting the sighting targets to the tested person via the driven and controlled wavefront corrector, to conduct a human eye visual function measurement process and a visual perception training process,
   wherein the video processing circuit combines the R channel and the B channel from a normal video output and obtains a grayscale of or higher than 14 bits.

2. The human eye adaptive optical visual perception training method according to claim 1, wherein
   the human eye visual function measurement process consists in a human eye contrast threshold measurement, where the difficulty of the stimulus is adjusted in real time in response to the reply from the tested person according to the adjustment method of psychophysics in such manner that the contrast of the sighting target to be displayed next is decreased if the number of continuous replies from the tested person that are correct reaches a first predetermined value, and the contrast is increased if the number of continuous replies that are wrong reaches a second predetermined value.

3. The human eye adaptive optical visual perception training method according to claim 2, wherein the correctness of the tested person during the whole measurement process maintains at a level through the adjustment and then a human eye contrast threshold of the tested person is obtained; and thereby a human eye contrast sensitivity is obtained by reversing the human eye contrast threshold.

4. The human eye adaptive optical visual perception training method according to claim 3, wherein the visual perception training process comprises steps of:

measuring a human eye contrast threshold of the tested person respectively for gratings of different spatial frequencies;

selecting a spatial frequency corresponding to a predetermined human eye contrast threshold based on the difference of the contrast thresholds under different spatial frequencies; and conducting the visual perception training process by using the grating with the selected spatial frequency.

5. The human eye adaptive optical visual perception training method according to claim 3, wherein the visual perception training process comprises steps of:

selecting the spatial frequency measured after the preceding visual perception training process; and conducting the visual perception training process by using the grating with the selected spatial frequency.

6. A human eye adaptive optical visual perception training apparatus, comprising:

a human eye wave aberration measurement sub-system including a near infrared reference light source, a wavefront corrector and a wavefront sensor, for measuring the human eye wave aberration of a person to be tested;

a human eye wave aberration correction sub-system including a control unit and said wavefront corrector, for driving and controlling the wavefront corrector to correct the human eye wave aberration of the person to be tested based on the measured human eye wave aberration of the tested person; and a visual perception training sub-system including a video processing circuit, a sighting target display and said wavefront corrector, for displaying on the sighting target display sighting targets of different spatial frequencies and different contrasts after they have been subjected to processing in the video processing circuit, and presenting the sighting targets to the tested person via the driven and controlled wavefront corrector, to conduct a human eye visual function measurement process and a visual perception training process, wherein the video processing circuit combines the R channel and the B channel from a normal video output and obtains a grayscale of or higher than 14 bits.

7. The human eye adaptive optical visual perception training apparatus according to claim 6, wherein the wavefront corrector is selected from a group consisted of a deformable reflective mirror, a liquid crystal wavefront corrector, a Micromachined membrane deformable mirror, a Microelectromechanical deformable mirror, a Bimorph deformable mirror and a liquid deformable mirror.

8. The human eye adaptive optical visual perception training apparatus according to claim 6, wherein the wavefront sensor is selected from a group consisted of a microlens-array-based Hartmann wavefront sensor, a microprism-array-based Hartmann wavefront sensor, a Curvature wavefront sensor and a Pyramid wavefront sensor.

9. The human eye adaptive optical visual perception training apparatus according to claim 6, wherein the sighting target display is selected from a group consisted of a CRT display, a commercial display, a liquid crystal display, a plasma display, an electro-luminescent display, and an organic luminescent display.

* * * * *